US012661396B2

(12) United States Patent
Lu et al.

(10) Patent No.: US 12,661,396 B2
(45) Date of Patent: Jun. 23, 2026

(54) SELECTIVE TARGETING OF THE TREML1/MD2 INTERACTION BY SMALL PEPTIDE OR PROTEIN AND ITS USE FOR VACCINE ADJUVANTS

(71) Applicant: Ascendo Biotechnology, Inc., Grand Cayman (KY)

(72) Inventors: Yen-Ta Lu, Taipei (TW); Chia-Ming Chang, Taipei (TW); Ping-Yen Huang, Taipei (TW); I-Fang Tsai, Taipei (TW)

(73) Assignee: Ascendo Biotechnology, Inc., Grand Cayman (KY)

( * ) Notice: Subject to any disclaimer, the term of this patent is extended or adjusted under 35 U.S.C. 154(b) by 661 days.

(21) Appl. No.: 17/998,733

(22) PCT Filed: May 14, 2021

(86) PCT No.: PCT/US2021/032620
§ 371 (c)(1),
(2) Date: Nov. 14, 2022

(87) PCT Pub. No.: WO2021/231971
PCT Pub. Date: Nov. 18, 2021

(65) Prior Publication Data
US 2023/0330222 A1 Oct. 19, 2023

Related U.S. Application Data

(60) Provisional application No. 63/025,152, filed on May 14, 2020.

(51) Int. Cl.
A61K 39/39 (2006.01)
A61P 37/04 (2006.01)
A61K 39/00 (2006.01)

(52) U.S. Cl.
CPC .............. *A61K 39/39* (2013.01); *A61P 37/04* (2018.01); *A61K 2039/55516* (2013.01); *A61K 2039/804* (2018.08)

(58) Field of Classification Search
None
See application file for complete search history.

(56) References Cited

U.S. PATENT DOCUMENTS

| | | |
|---|---|---|
| 2004/0180409 A1 | 9/2004 | McVicar et al. |
| 2008/0145375 A1 | 6/2008 | Bembridge et al. |
| 2016/0015773 A1 | 1/2016 | Gibot et al. |

FOREIGN PATENT DOCUMENTS

| | | |
|---|---|---|
| CN | 103153327 A | 6/2013 |
| CN | 108135961 A | 6/2018 |
| JP | 2018524299 A | 8/2018 |
| WO | WO2010132370 A2 | 11/2010 |
| WO | WO2011/023785 A1 | 3/2011 |
| WO | WO2016197975 A1 | 12/2016 |

OTHER PUBLICATIONS

International Search Report and Written Opinion mailed Oct. 7, 2021 in International Application No. PCT/US2021/032620, 11 pages.
Canadian Office Action mailed Jan. 3, 2024 for Canadian Application No. 3,173,603, a foreign counterpart to U.S. Appl. No. 17/998,733, 4 pages.
Office Action for Canadian Application No. 3,173,603, Dated Jan. 3, 2024, 4 pages.
Search Report and Written Opinion for European Application No. 21803868.5, Dated Jun. 7, 2024, 7 pages.
Office Action for Canadian Application No. 3,173,603, Dated Apr. 2, 2025, 4 pages.
Office Action for Chinese Application No. 202180034226.1, Dated Apr. 16, 2025, 14 pages.
Das, et al., "Elevated level of circulatory sTLT1 induces inflammation through SYK/MEK/ERK signaling in coronary artery disease", Clinical Science, vol. 133, Issue 22, Nov. 2019, pp. 2283-2299.
Office Action for European Application No. 21803868.5, Dated Jul. 30, 2025, 4 pages.
Gattis, et al., "The Structure of the Extracellular Domain of Triggering Receptor Expressed on Myeloid Cells Like Transcript-1 and Evidence for a Naturally Occurring Soluble Fragment," The Journal of Biological Chemistry, vol. 281, No. 19, May 27, 2006, pp. 13396-13403.
Office Action for Japanese Application No. 2022-569225, Dated Aug. 5, 2025, 10 pages.
Office Action for Chinese Application No. 202180034226.1, dated Dec. 26, 2025, 16 pages.
Office Action for Chinese Application No. 202180034226.1, dated Mar. 12, 2026, 16 pages.
Office Action for Japanese Application No. 2022-569225, Dated Mar. 10, 2026, 7 pages.

*Primary Examiner* — Brad Duffy
(74) *Attorney, Agent, or Firm* — Lee & Hayes, P.C.

(57) ABSTRACT

A pharmaceutical composition for boosting an immune response contains TREM-like transcript-1 (TREML1) extracellular domain (ECD) or stalk polypeptide. The TREML1 ECD or stalk polypeptide is derived from human or mouse TREML1. The pharmaceutical composition further contains an antigen as a vaccine, wherein the TREML1 ECD or stalk polypeptide functions as an adjuvant or immune booster.

15 Claims, 7 Drawing Sheets
Specification includes a Sequence Listing.

human MD2 binding to TREML1 stalk mouse MD2 binding to mTREML1 stalk

TREML1 ECD binding to THP1/XBlue/MD2/CD14

Tumor growth (Day 27)

SELECTIVE TARGETING OF THE TREML1/MD2 INTERACTION BY SMALL PEPTIDE OR PROTEIN AND ITS USE FOR VACCINE ADJUVANTS

CROSS-REFERENCE TO RELATED APPLICATIONS

This application is a U.S. National phase of International Application No. PCT/US2021/032620, filed May 14, 2021, which claims benefit of U.S. Provisional Application No. 63/025,152, filed May 14, 2020, which are both incorporated herein by reference in their entirety.

FIELD OF INVENTION

The present invention relates to polypeptide fragments derived from the TREM-like transcript-1 (TREML1; TLT-1) protein and peptide fragments and their uses as vaccine adjuvants or immune boosters or TLRs (Toll-like receptors) agonists.

BACKGROUND OF INVENTION

TREML1 is exclusively found in platelets in the periph-eral blood of humans. Upon platelet activation, TREML1 is quickly exposed on the membrane of platelets and subse-quently cleaved, leading to the release of a soluble fragment (sTREML1). Studies showed that patients with sepsis, in contrast to healthy individuals, have increased levels of soluble TREML1 in the plasma. Patients who died of sepsis had sustained high levels of soluble TREML1 in the plasma, whereas those who survived sepsis showed reduced levels of soluble TREML1 in the plasma. In other diseases, such as acute respiratory distress syndrome (ARDS), acute coronary syndrome, and coronary artery disease, high levels of soluble TREML1 plasma concentration have also been shown to be associated with negative outcomes. Thus, monitoring soluble TREML1 levels in the plasma could be an important prognostic indicator. We previously found that soluble TREML1 can directly bind to monocytes and modu-late immune responses (WO2016197975A1). These results suggested that soluble TREML1 plays an important role in the inflammatory related disease.

MD2 (LY-96, lymphocyte antigen 96) appears to associate with toll-like receptor 4 (TLR4) on the cell surface and confers responsiveness to a wide variety of endotoxic lipopolysaccharides (LPS), thus providing a link between the receptor and LPS signaling. However, it is unclear whether MD2 and TLR4 can bind other endogenous proteins to enable TLR signaling.

SUMMARY OF THE INVENTION

Embodiments of the present invention are based on unex-pected finding that TREML1 extracellular domain (ECD) or its stalk can bind to TLR4/MD2 complex, leading to modu-lation of TLR4 signaling. In addition, TREML1 ECD can also enhance cellular responses medicated by TLR7/8/9 agonist. As a result of TREML1 ECD or its stalk binding to the TLR4/MD2 complex, TREML1 ECD or its stalk can induce dendritic cell activation and maturation. Therefore, TREML1 ECD or its stalk can serve as a vaccine adjuvant or an immune booster or as a TLR agonist.

One aspect of the invention relates to pharmaceutical compositions for boosting immune responses. A pharmaceu-tical composition in accordance with one embodiment of the invention includes contains TREM-like transcript-1 (TREML1) extracellular domain (ECD) or stalk polypep-tide. The TREML1 ECD or stalk polypeptide may be derived from human or mouse TREML1. The TREML1 ECD or TREML1 stalk polypeptide has the amino-acid sequence of SEQ ID NO:1, SEQ ID NO:2, SEQ ID NO:3, or SEQ ID NO:4.

In accordance with some embodiments of the invention, the pharmaceutical composition further comprises a TLR agonist. Examples of TLR agonists include lipopolysaccha-rides, heat shock proteins, fibrinogen, heparan sulfate frag-ments, hyaluronic acid fragments, CpG (CpG-ODNs (CpG oligodeoxynucleotides), D-W Yeh et al., "CpG-oligodeoxy-nucleotides developed for grouper toll-like receptor (TLR) 21s effectively activate mouse and human TLR9s mediated immune responses," *Sci Rep,* 2017, 7(1):17297), R848 (4-amino-2-(ethoxymethyl)-α,α-dimethyl-1H-imidazo[4,5-c]quinoline-1-ethanol, ACS #144875-48-9) and various opi-oid drugs (e.g., morphine, remifentanil; M. R Hutchinson et al., "Opioid Activation of Toll-Like Receptor 4 Contributes to Drug Reinforcement," *J. Neuorosci.,* 2012, 32(33): 11187-11200). In accordance with some embodiments of the invention, a pharmaceutical composition may further con-tain an antigen as a vaccine, wherein the TREML1 ECD or stalk polypeptide functions as an adjuvant or immune booster. The antigen may be a marker for a cancer. The cancer may be colorectal cancer, breast cancer, lung cancer, melanoma, hepatoma, head and neck cancers, squamous cell carcinomas of the lung, ovarian cancer, uterine cancer, prostate cancer, gastric carcinoma, cervical cancer, esopha-geal carcinoma, bladder cancer, kidney cancer, brain cancer, bone cancer, pancreatic cancer, skin cancer, cutaneous or intraocular malignant melanoma, rectal cancer, cancer of the anal region, stomach cancer, testicular cancer, carcinoma of the fallopian tubes, carcinoma of the endometrium, carci-noma of the cervix, carcinoma of the vagina, carcinoma of the vulva, Hodgkin's Disease, non-Hodgkin's lymphoma, esophagus cancer, small intestine cancer, endocrine system cancer, thyroid gland cancer, parathyroid gland cancer, adre-nal gland cancer, sarcoma of soft tissue, urethra cancer, penis cancer, chronic or acute leukemias including acute myeloid leukemia, chronic myeloid leukemia, acute lym-phoblastic leukemia, chronic lymphocytic leukemia, solid tumors of childhood, lymphocytic lymphoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, medulloblastoma pilomatrixomas, endometrial cancer, mul-tiple myeloma, or T-cell lymphoma.

One aspect of the invention relates to methods for boost-ing immune responses. A method in accordance with one embodiment of the invention comprises administering any one of the above pharmaceutical composition to a subject in need thereof.

Other aspects of the invention would be apparent with the following description and the accompanying drawings.

3

184-313 of TREML1, contains an immune tyrosine inhibitory motif (ITIM; residues 279-284).

Figure 2:
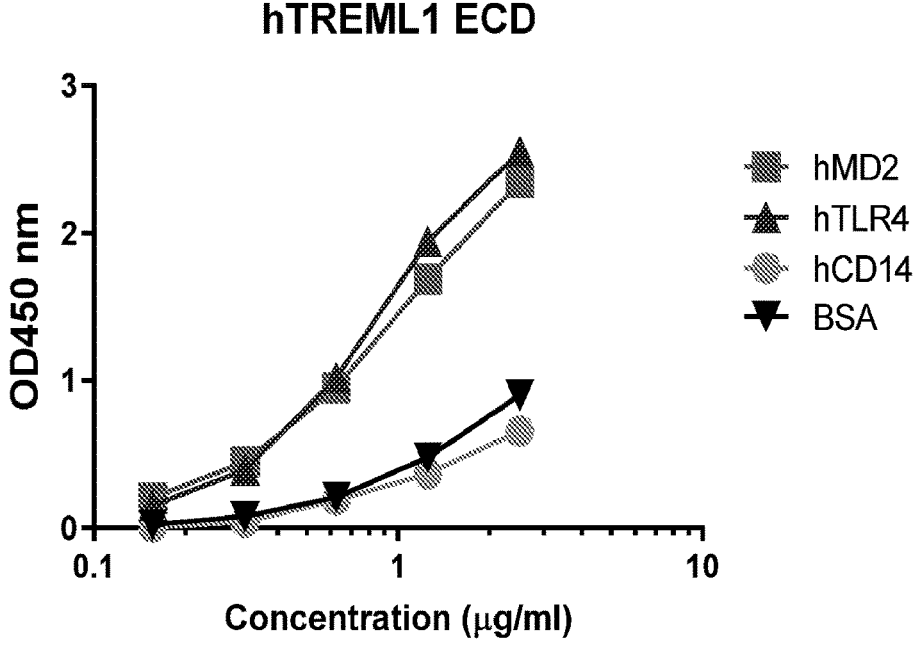

FIG. 2 shows results from binding of TREML1 ECD to various candidate proteins. The results show that recombinant TREML1 ECD can bind to the immobilized MD2 and TLR4 in the solid phase binding assays.

Figure 3A:
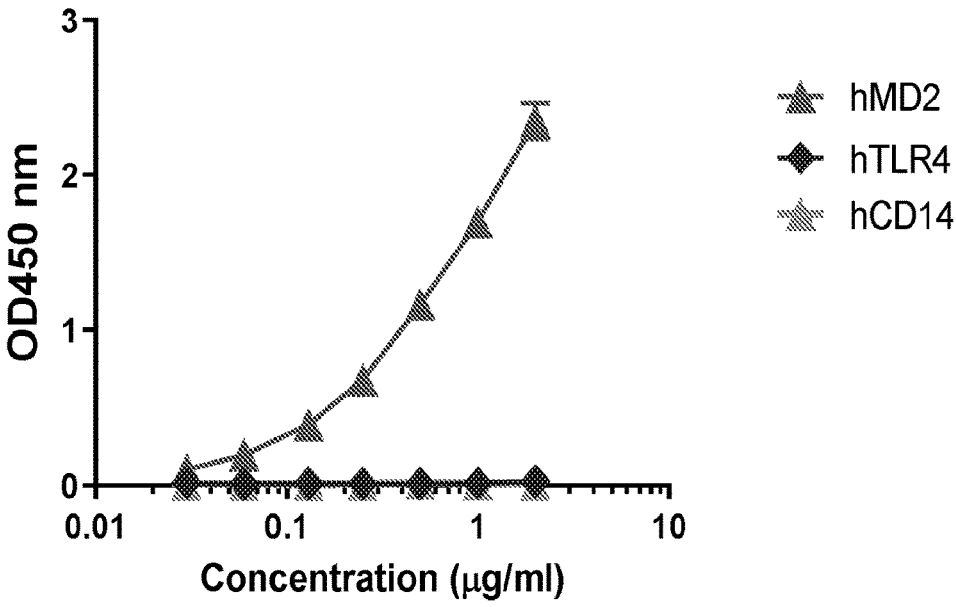
Figure 3B:
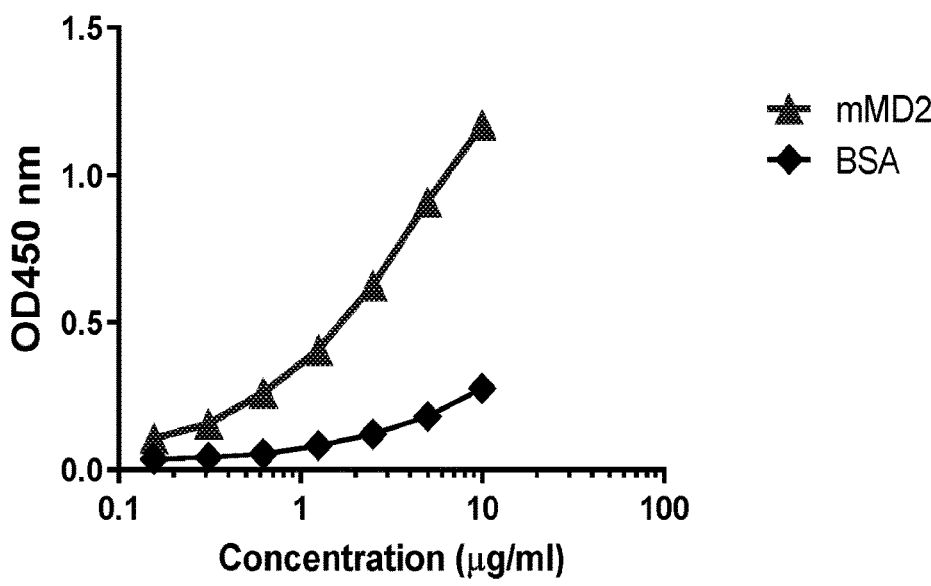

FIG. 3A and FIG. 3B show results of MD2 binding to various proteins. The results show that human and mouse MD2 protein can bind to the immobilized TREML1 stalk and mTREML1 stalk, respectively, in the solid phase binding assays.

Figure 4:
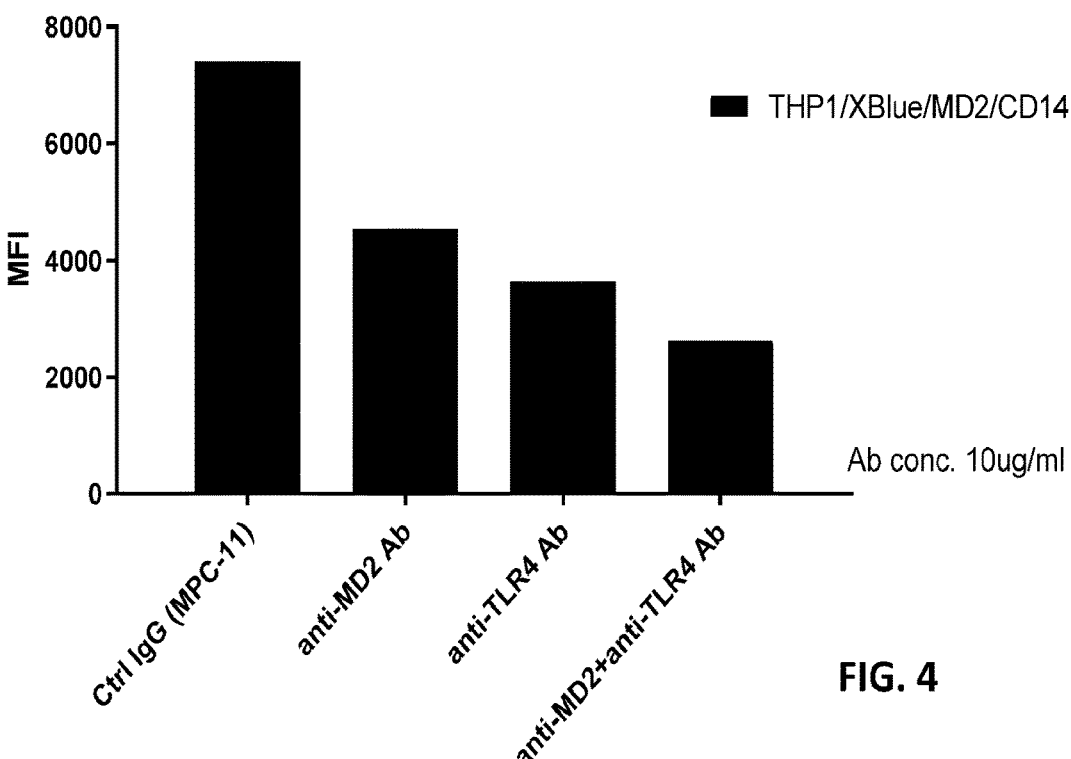

FIG. 4 shows results of various antibodies competing with TREML1 ECD binding to THP1/XBlue/MD2/CD14, which expresses MD2 and CD14. THP1 is derived from human monocytes that naturally express many pattern-recognition receptors, including Toll-like receptors. Both MD2 and CD14 are co-receptors of TLR4 and mediate LPS-induced responses. The results show that anti-MD2 antibody (18H10) and anti-TLR4 antibody (HTA125) can compete with TREML1 ECD binding to THP1/XBlue/MD2/CD14 monocytes.

Figure 5A:
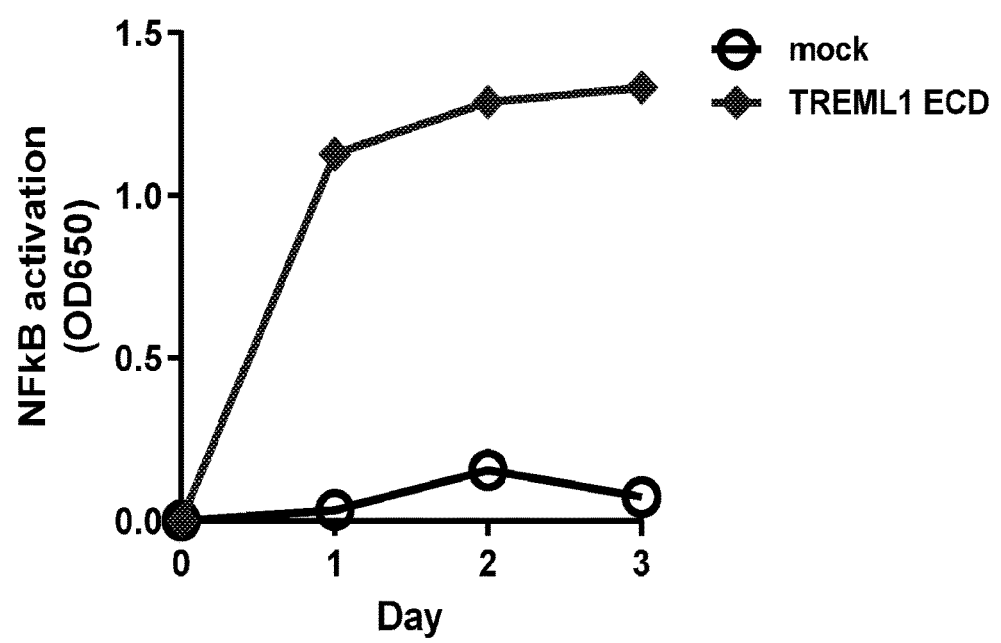
Figure 5B:
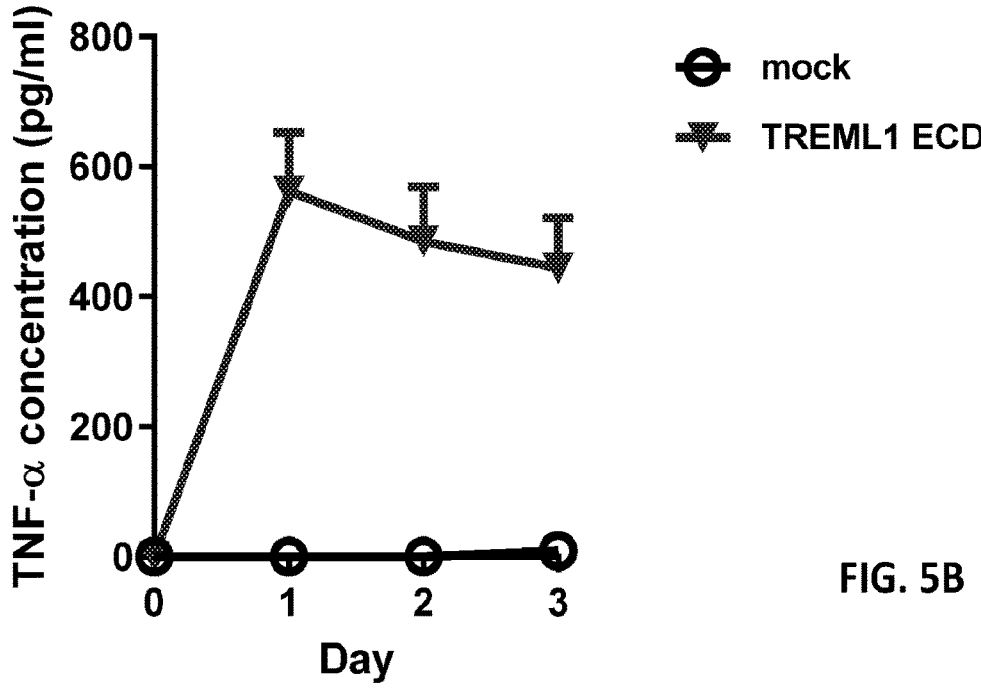

FIGS. 5A and 5B show that TREML1 ECD can induce THP1/XBlue/MD2/CD14 monocyte activation. FIG. 5A shows TREML1 ECD-induced NF-κB secretion upon activation of THP1/XBlue/MD2/CD14, and FIG. 5B shows TREML1 ECD-induced TNF-α secretion upon activation of THP1/XBlue/MD2/CD14.

Figure 6:
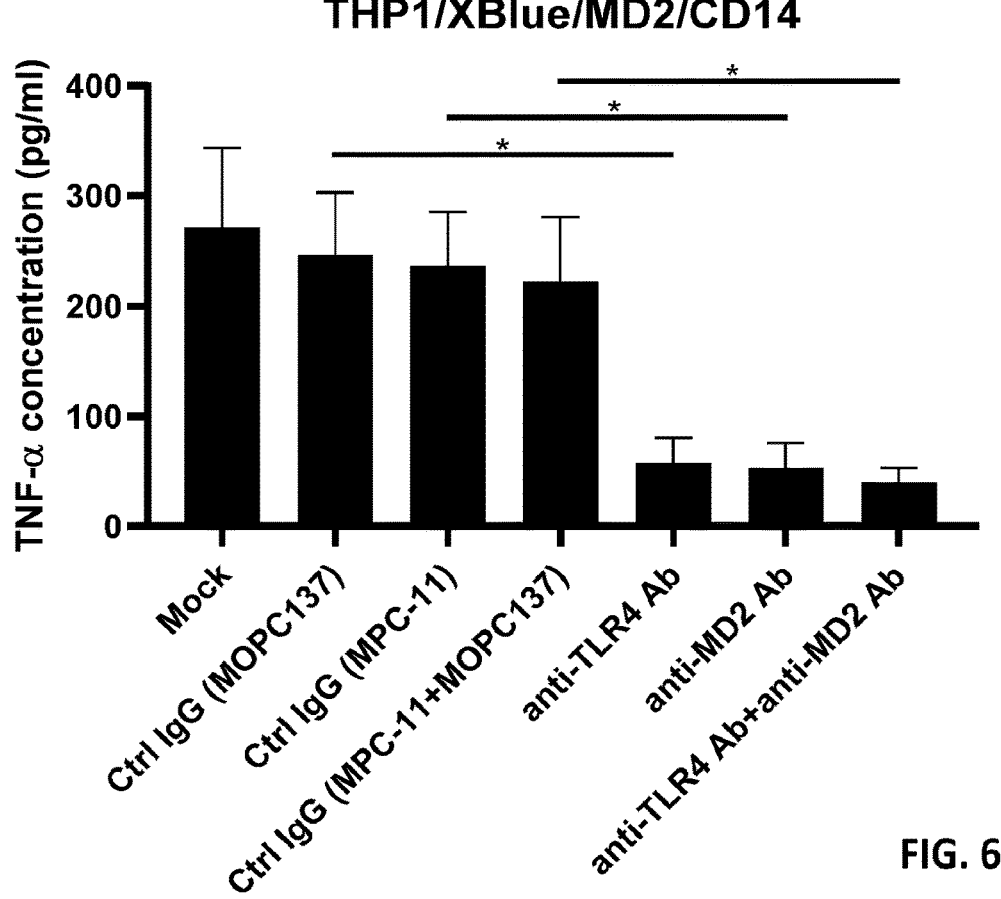

FIG. 6 shows that anti-MD2 antibody (18H10) and anti-TLR4 antibody (HTA125) treatment reduce TREML1 ECD-induced THP1/XBlue/MD2/CD14 monocyte activation, as evidenced by reduced TNF-α secretion.

Figure 7A:
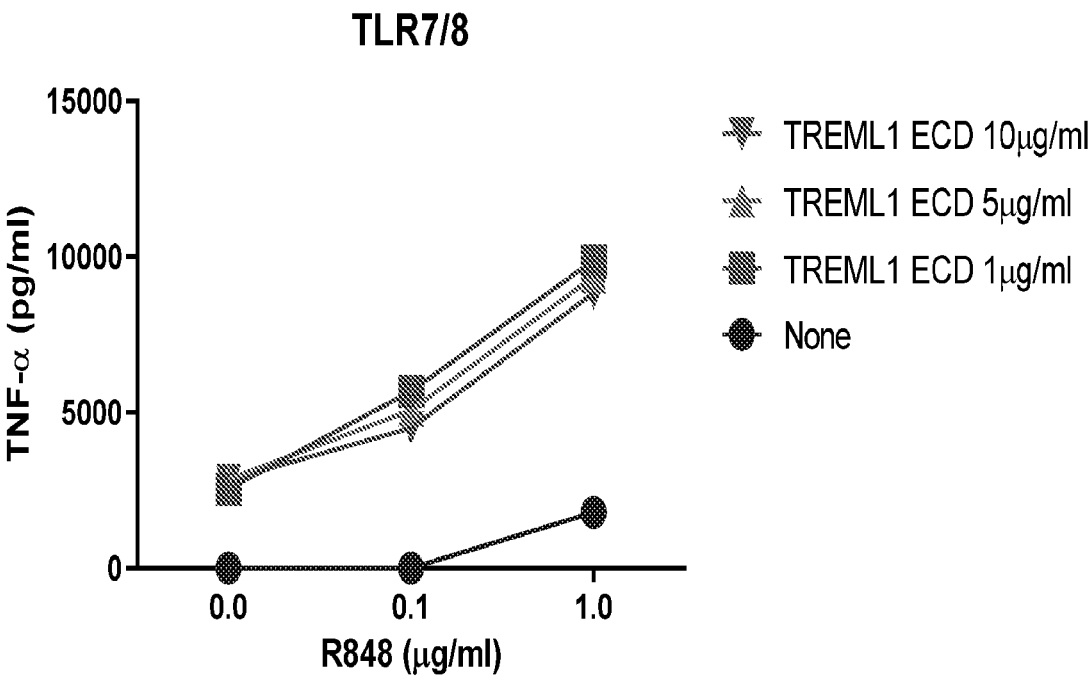
Figure 7B:
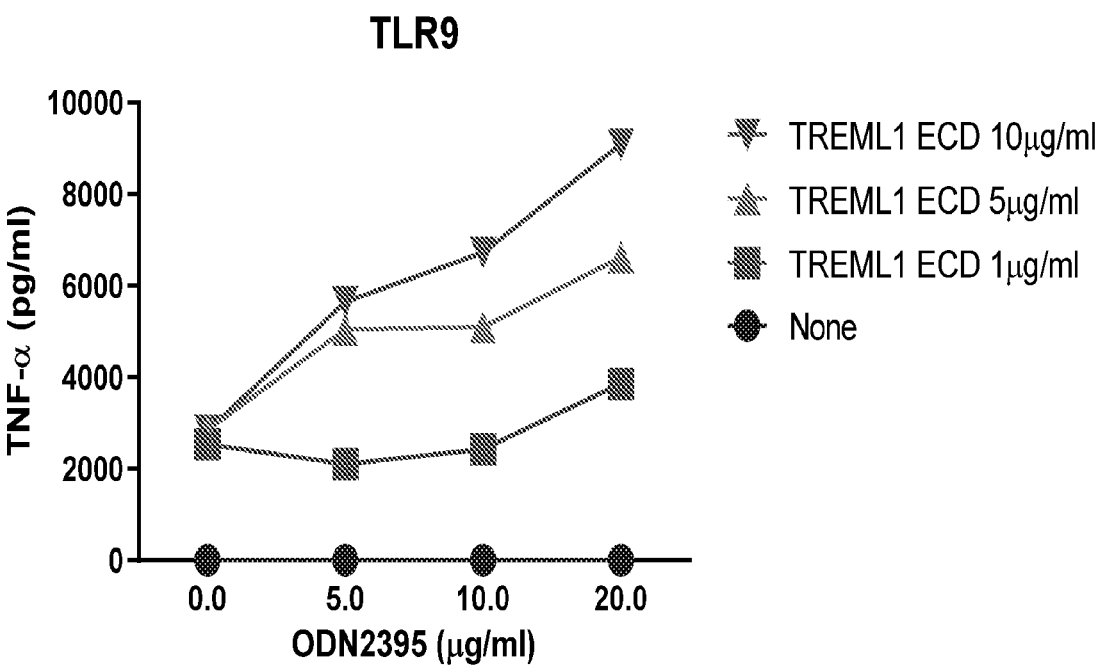

FIGS. 7A and 7B show that TREML1 ECD can enhance intracellular TLR (i.e., TLR7, TLR8, and TLR9)-induced cell activation.

Figure 8:
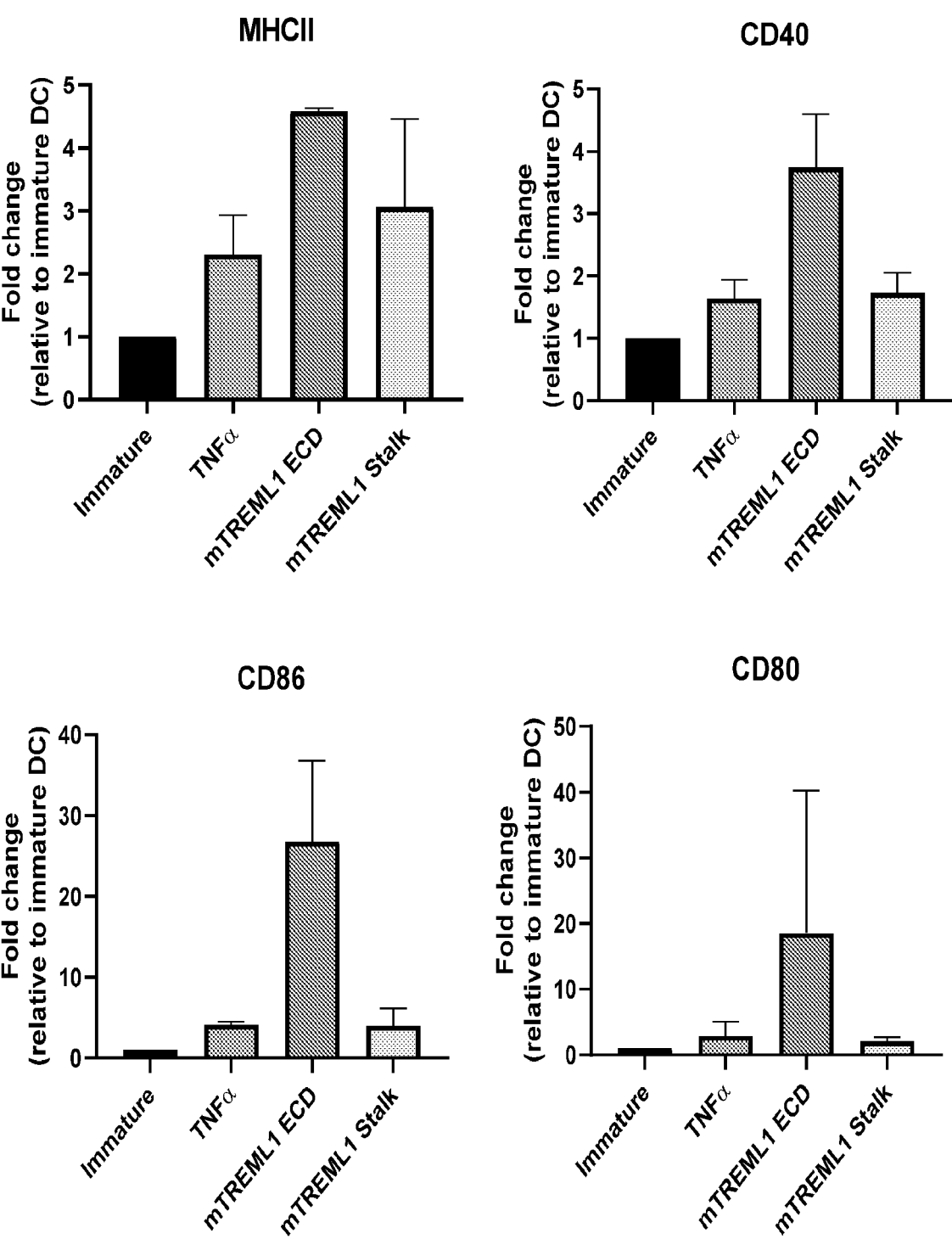

FIG. 8 shows that mTREML1 ECD and mTREML1 stalk peptide can trigger dendritic cell maturation.

Figure 9A:
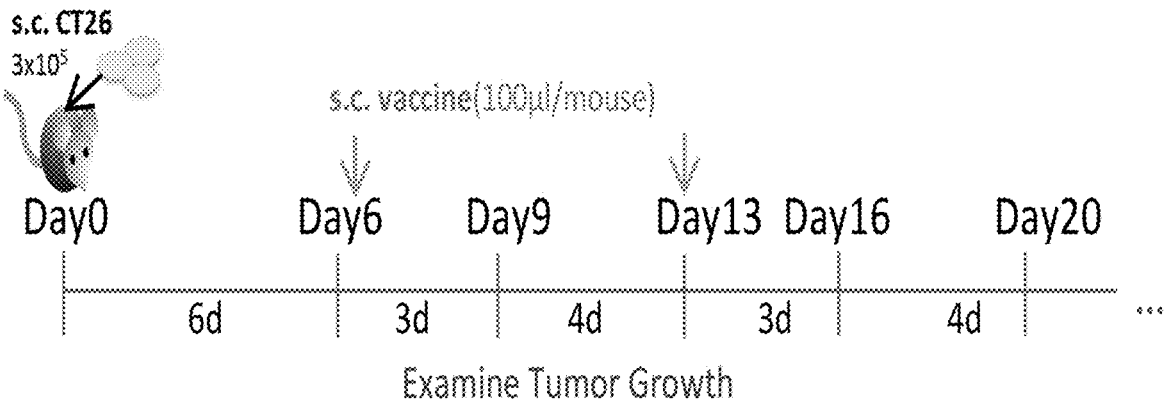
Figure 9B:
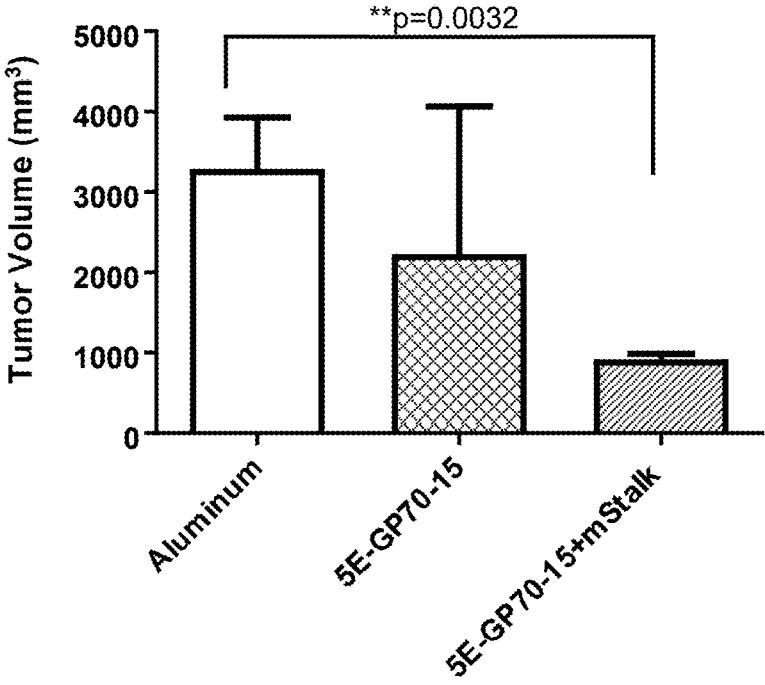

FIG. 9A shows a treatment schedule in an animal model for testing the effect of TREML1 stalk as an adjuvant of a cancer vaccine. FIG. 9B shows that mTREML1 stalk as adjuvants enhance the efficacy of cancer vaccines.

DETAILED DESCRIPTION

Embodiments of the invention relate to TREML1 ECD or stalk peptides derived from TREML1 for use as an immune booster or a TLRs agonist. Inventors of the invention unexpectedly found that TREML1 ECD or its stalk can bind to MD2, which can associate with toll-like receptor 4 (TLR4) on the cell surface. MD2 interacts with TLR4 to confer responsiveness to a wide variety of stimuli, such as endotoxic lipopolysaccharides (LPS). TLR4 activation leads to intracellular signaling that increases NF-kB and inflammatory cytokine (e.g., TNF-α) production, which is responsible for activating the innate immune responses. In addition, TREML1 ECD or its stalk is also found to interact with TLR2, 7, 8, or 9. The interactions between TREML1 ECD or its stalk and TLR2/7/8/9 result in dendritic cell (DC) activation and maturation, further boosting immune responses.

Figure 1:
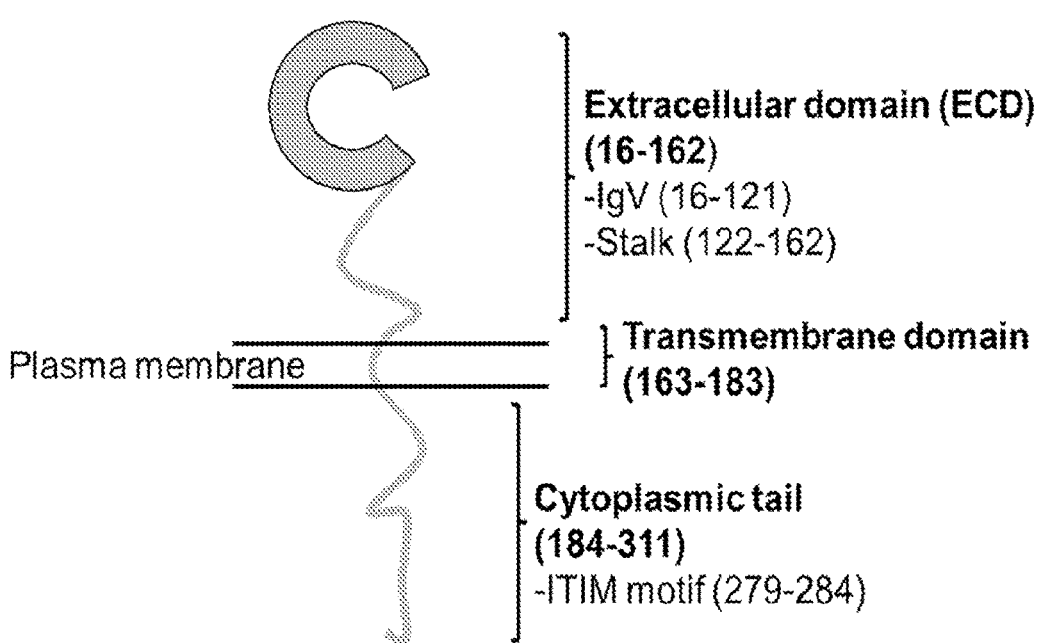
FIG. 1 shows a schematic of TREML1, illustrating an extracellular domain (ECD), a transmembrane domain, and a cytoplasmic domain. The ECD spans residue 16 to residue 162 of TREML1, and the transmembrane domain spans residues 163-183 of TREML1. The ECD comprises a single IgV domain (residues 16-121) and a stalk region (residues 122-162). The cytoplasmic domain, which spans residues

TREM-like transcript-1 (TREML1) is a member of the TREM family. As shown in FIG. 1, TREML1 is a single transmembrane protein, consisting of an extracellular domain (ECD, residues 16-162), a transmembrane domain (TMD, residues 163-183), and a cytoplasmic domain (residues 184-311) that comprises an immune tyrosine inhibitory motif (ITIM, residues 279-284). The ECD of TREML1 comprises a single V-set immunoglobulin (Ig) domain (residues 16-121) and a stalk region (residues 122-162).

To identify potential binding partners of TREML1 ECD, we used solid phase binding assay to assess interactions between TREML1 ECD and candidate proteins. Briefly, various candidate proteins and BSA (as a negative control) were coated on a 96-well plate and TREML1 ECD at various concentrations were added to the wells. After binding and washing, an anti-TREML1 antibody conjugated with horse radish peroxidase (HRP) was added to each well. After washing, HRP substrate, TMB (3,3',5,5'-tetramethylbenzidine), was added. After reaction, absorbance at 450 nm was measured to assess TREML1 binding. An exemplary set of results is shown in FIG. 2, in which recombinant TREML1 ECD binds MD2 and TLR4 in a concentration-dependent manner. In contrast, TREML1 ECD does not bind to CD14 or BSA.

Furthermore, MD2 (LY96) binds with TREML1 stalk in a concentration-dependent manner. In contrast, TLR4 and CD14 do not bind TREML1 stalk (FIGS. 3A and 3B). Like MD2, CD14 also acts as a co-receptor (along with the Toll-like receptor TLR 4) for the detection of bacterial lipopolysaccharides (LPS). These results indicate that TREML1 stalk binds directly with MD2 in the CD14/MD2/TLR4 receptor complex.

In addition to the solid phase binding assays, the TREML1 ECD binding was further evaluated using THP1/XBlue/MD2/CD14 cells (InvivoGen, San Diego, USA), which express MD2 and CD14. These cells (InvivoGen, San Diego, USA) are derived from the human monocytic THP1 cell line and express an NF-κB- and AP-1-inducible secreted embryonic alkaline phosphatase (SEAP) reporter gene.

As shown in FIG. 4, TREML1 ECD can bind to the THP1/XBlue/MD2/CD14 cells. The binding test was also confirmed using an anti-MD2 antibody (18H10) and anti-TLR4 antibody (HTA125) to compete with TREML1 binding to the THP1/XBlue/MD2/CD14 cells. The results of the binding competition are shown in FIG. 4. Anti-MD2 antibody and anti-TLR4 antibody are able to compete with TREML1 binding to the THP1/XBlue/MD2/CD14 cells, and a combination of anti-MD2 and anti-TLR4 antibodies produces an additive effect.

Binding to TLR4/MD2 expressed by the THP1/XBlue/MD2/CD14 cells by TREML1 ECD suggests that TREML1 ECD should be able to activate monocytes. Indeed, as shown in FIGS. 5A and 5B, TREML1 ECD induces THP1/XBlue/MD2/CD14 monocyte activation, as evidenced by the induced activation of NF-κB (FIG. 5A) and TNF-α (FIG. 5B) secretions.

THP1/XBlue/MD2/CD14 monocyte activation by TREML1 is mediated by MD2 and TLR4, as evidenced by the ability of anti-MD2 antibody (18H10) and anti-TLR4 antibody (HTA125) to inhibit TREML1-induced TNF-α secretion. FIG. 6 shows that TREML1-induced TNF-α secretion is specifically inhibited by anti-MD2 antibody (18H10), anti-TLR4 antibody (HTA125) or a combination thereof, whereas control IgGs (MOPC137 and/or MPC-11) do not have this effect.

The TLR family plays an important role in pathogen recognition and activation of innate immunity. They recognize pathogen-associated molecular patterns (PAMPs) that are expressed on infectious agents and mediate the production of cytokines necessary for the development of effective immunity. The various TLRs exhibit different patterns of expression and may mediate different functions.

In addition to exerting functions through TLR4, we also found that that TREML1 ECD can enhance intracellular TLR (i.e., TLR7, TLR8, and TLR9)-induced cell activation. For example, FIG. 7A shows that an agonist of R848 (TLR7 and TLR8 agonist) can induce TNF-α secretion. The R848-induced TNF-α secretion mediated by TLR7/8 is enhanced in the presence of TREML1 ECD. Similar results were observed for TLR9. As shown in FIG. 7B, the ODN 2395 (TLR9 agonist)-induced TNF-α secretion is enhanced in the presence of TREML1 ECD in a dose-dependent manner. These results indicate that TREML1 ECD or stalk peptides can be used as agonists of TLR receptors. As agonists of these receptors, TREML1 ECD or stalk peptides can enhance the innate immune responses.

The capacity of dendritic cells (DC) to regulate adaptive immunity is controlled by their maturation state and lifespan. TNF is a well-known maturation and survival factor for DC. We found that TREML1 is an even more potent factor for DC maturation. As shown in FIG. 8, mouse TREML1 (mTREML1) ECD and mTREML1 stalk peptide can trigger dendritic cell maturation, as evidenced by the increased levels of DC maturation markers CD40, CD86, CD80, and MHC II. The effects of TREML1 ECD or its stalk peptide are significantly stronger than those of TNF-α. These results indicate that TREML1 ECD or stalk peptides can also enhance the adaptive immune responses, in addition to enhancing the innate immune responses.

The above results together indicate that TREML1 ECD or TREML1 stalk can interact with MD2/TLR4, enhance TLR7, TLR8, and TLR9 activation, and trigger DC maturation. TLRs are key regulators of both innate and adaptive immune responses. (Hayden M S, West A P, Ghosh S (October 2006). "NF-κB and the immune response". *Oncogene*. 25 (51): 6758-80). The interactions between TREML1 ECD (or its stalk) and MD2/TLR4 or TLR7/8/9 lead to activation of NF-κB and TNF-α secretion.

The primary role of TNF-α is in the regulation of immune cells. NF-κB is a major transcription factor that regulates genes responsible for both the innate and adaptive immune responses. Upon activation of either the T- or B-cell receptors, NF-κB becomes activated by distinct signaling components. Through a cascade of phosphorylation events, the kinase complex is activated and NF-κB enters the nucleus to upregulate genes involved in T-cell development, maturation, and proliferation. Thus, interactions between TREML1 ECD or stalk and MD2/TLR4 can boost both innate and adaptive immune responses. In this regard, certain TLR4 agonists have been used as immunomodulators or as vaccine adjuvants. For example, MPL (monophosphoryl lipid A, a detoxified form of lipopolysaccharide) is used in marketed vaccine formulations.

Furthermore, interactions between TREML1 ECD or stalk and TLR4/MD2 results in enhancement of TLR7/8/9 induced cell activations. These effects together enhance the activation and maturation of dendritic cells (DC). The abilities to work through both the TLR4/MD2 system and the TLR7/8/9 system suggest that TREML1 ECD or its stalk would be potent immune boosters. Based on these novel findings, embodiments of the invention relate to reagents and methods for boosting immune responses using TREML1 ECD or its stalk. Thus, TREML1 ECD or its stalk may be used in vaccines to boost immune responses in a manner similar to an adjuvant. As an adjuvant or immune booster, a TREML1 ECD or its stalk peptide can be used with an antigen, with or without another adjuvant or another TLR receptor agonist.

To test TREML1 ECD or its stalk as a vaccine adjuvant or immune booster, we use a CT26 colon carcinoma animal model. FIG. 9A shows the experimental protocol for this study. Briefly, CT26 colon cancer cells ($3\times10^5$ cells) were injected subcutaneously into BALB/c mice on day 0. When the tumor grows to 30-100 mm$^3$ on day 6, tumor vaccines (tumor antigen 5E-GP70-15/aluminum mixture with or without mouse TREML1 stalk; 100 μL/mouse each time) were injected subcutaneously. The vaccinations were repeated on days 13. Tumor volumes were measured every 3-4 days. GP70 is an endogenous ecotropic murine leukemia virus that is comparable to human tumor-associated antigens. A DNA vaccine containing the gp70 gene has been used to induce protective immunity against CT26 cells. (J. Takeda et al., "Anti-tumor immunity against CT26 colon tumor in mice immunized with plasmid DNA encoding beta-galactosidase fused to an envelope protein of endogenous retrovirus," *Cell Immunol.*, (2000), 204(1): 11-18).

As shown in FIG. 9B, while treatment with tumor antigen 5E-GP70-15/aluminum mixture only reduced tumor volume slightly, as compared to the control group (treatment with aluminum alone), the combination of tumor antigen 5E-GP70-15/aluminum mixture and mTREML1 stalk produced a dramatic reduction in the tumor volumes. These results indicate that TREML1 stalk can substantially enhance the vaccine efficacy by boosting immune responses. The unexpectedly strong immune response boost by TREML1 ECD or stalk is likely due to the combination effects on both the innate and adaptive immune systems, i.e., induction of maturation of antigen-presenting cells (APCs) by the TREML1 ECD or stalk, as well as interactions of TREML1 ECD or stalk with TLR4/MD2 and/or TLR7/8/9, as described above.

In accordance with embodiments of the invention, a TREML1 ECD or stalk peptide can be used alone as a TLR agonist to enhance the innate immune response. In addition, a TREML1 ECD or stalk peptide can be used as an adjuvant or immune booster together with an antigen in vaccinations or immunotherapies, with or without another adjuvant (e.g., alum) or another TLR agonist (e.g., monophosphoryl lipid A). These TREML1 ECD or stalk peptides can be used in immunotherapies to treat cancers without being limited to any specific tumors or vaccines due to their mechanism of action, which is similar to an adjuvant. However, TREML1 ECD or stalk peptides are expected to be more effective than a conventional adjuvant because they can function as TLR agonists and can enhance both innate and adaptive immune responses. For these reasons, TREML1 ECD or stalk peptides, as general immune boosters, can be used in vaccinations or immunotherapies of all kinds, including tumor immunotherapies. Example of tumors and vaccines that TREML1 ECD or stalk peptides can be used in include, but are not limited to, colorectal tumor (gp70-15 vaccine, carcinoembryonic antigen (CEA) vaccine, MUC-1 vaccine, beta human chorionic gonadotrophin (β-hCG) vaccine, guanylyl cyclase C (GUCY2C) vaccine, epithelial growth factor receptor (EGFR) vaccine, epithelial cell adhesion molecule (EpCAM) vaccine), breast cancer (MUC-1 vaccine, surviving vaccine, telomerase vaccine and epithelial tumor antigen vaccine), hepatocellular carcinoma (alpha fetoprotein vaccine), ovarian cancer (CA-125), malignant melanoma (tyrosinase vaccine, and melanoma-associated antigen vaccine), virus-induced tumor (HPV type 16 and 18 E6/E7, HBV, HCV, EBV vaccine) and various tumors (RAS vaccine, p53 vaccine, β-catenin vaccine, CDK4 genes BCR-ABL protein vaccine, personalized genomic vaccine and neoantigen personalized vaccine).

The TREML1 ECD or stalk peptides for use with embodiments of the invention may be derived from human TREML1, mouse TREML1, or other animal TREML1. Some examples of the TREML1 proteins or peptides used in the embodiments of the invention are shown in Table I:

TABLE I

Peptides used in the invention.

| Poly-peptide name | Peptide used Sequence | SEQ ID NO |
|---|---|---|
| TREML1 ECD | QGIVGSLPEVLQAPVGSSILVQCHYRLQ DVKAQKVWCRFLPEGCQPLVSSAVDRRA PAGRRTFLTDLGGGLLQVEMVTLQEEDA GEYGCMVDGARGPQILHRVSLNILPPEE EEETHKIGSLAENAFSDPAGSANPLEPS QDEKSIP | 1 |
| mTREML1 ECD | DSHPEVLQAPVGSSILVQCHYRLQDVRA LKVWCQFLQEGCHPLVTSAVDRRAPGNG RIFLTDLGGGLLQVEMVTLQEEDTGEYG CVVEGAAGPQTLHRVSLLVLPPVPGPRE GEEAEDEKETYRIGTGSLLEDPSLDPSA SAGPHEFRRRENSIP | 2 |
| TREML1 stalk | ILPPEEEEETHKIGSLAENAFSDPAGSA NPLEPSQDEKSIP | 3 |
| mTREML1 stalk | EGEEAEDEKETYRIGTGSLLEDPSLDPS ASAGPHEFRRRENSIP | 4 |
| 5E-GP70-15 | EEEEETYHSPSYVYHQFERR | 5 |

Embodiments of the invention will be further illustrated with the following specific examples. One skilled in the art would appreciate that these examples are for illustration only and that other modifications and variations are possible without departing from the scope of the invention.

Material and Method

Generation of Recombinant TREML1 ECD and TREML1 Stalk Polypeptide

Proteins and peptides for use with embodiments of the invention may be generated with recombinant techniques or chemical synthesis known in the art. For example, to generate recombinant TREML1 ECD, pET30-TREML1 encoding a human or mouse TREML1 ECD (SEQ ID NO:1 and SEQ ID NO:2) with a polyhistidine tag at the N-terminus was expressed using *E. coli* and purified using Ni-NTA columns (Novagen). The purity of the recombinant protein was determined using sodium dodecyl sulfate polyacrylamide gel electrophoresis (SDS-PAGE) and visualized using a Coomassie blue stain was >95%. The endotoxin contamination of the purified proteins was examined using a LAL assay (QCL-1000; Charles River Laboratories, Wilmington, Massachusetts, USA). All proteins were sterile, and the endotoxin concentrations were lower than the detectable limit (<0.1 EU/μg protein). The TREML1 stalk polypeptides were chemically synthesized by Kelowna International Scientific Inc. (Taipei, Taiwan).

Solid-Phase Binding Assays

To investigate the protein-protein interactions. Recombinant TLR4 (5 ug/ml in PBS), MD2 (5 ug/ml in PBS), CD14 (5 ug/ml in PBS), and BSA (negative control) proteins were plated separately on 96-well plates and incubated overnight at 4 degrees Celsius. The blocking buffer (2% BSA in PBS) was added to avoid the nonspecific binding for 2 hr at room temperature. A serial diluted TREML1 ECD (2.5 ug/ml to 156 ng/ml, 2-fold dilutions) solutions were added and allowed to incubate at room temperature for 2 hr. Then, anti-TREML1 antibody (1 ug/ml in PBS) was added for 1 hr. Next, a secondary antibody with HRP labeling, anti-Rat IgG-HRP, was added to the plates and incubated for 30 minutes at room temperature. Plates were washed three times with 0.05% tween20 of PBS buffer (PBST) between each step. Finally, TMB substrate was added and incubated for 10-15 min to detect HRP-labeled antibody. After that, a stop solution of 1N HCL was added to stop the reaction. Absorbance at OD450/540 nm was measured with a microplate reader.

For TREML1 or mTREML1 stalk binding to human or mouse MD2 protein, TREML1 stalk or mTREML1 stalk (5 ug/ml in PBS) was coated separately on a 96-well plate. Recombinant hTLR4, hMD2, hCD14, or mMD2 was each serially diluted and added to the plates. Anti-His tag antibody-HRP was used as a detection antibody to detect the protein binding.

Preparation of Human White Blood Cells

Human peripheral blood samples from healthy volunteer donors were collected by venipuncture bled into ACD vacutainer tubes. Human peripheral blood mononuclear cells (PBMCs), which were separated from whole blood using Ficoll-Paque Plus (GE17-1440-03) according to the manufacturer's instructions.

Human peripheral blood mononuclear cells (PBMCs) were pretreated with or without hTREML1 (10 ug/ml, 5 ug/ml and 1 ug/ml) and incubated for 30 min at 37° C. with 5% $CO_2$. After treatments, cells were stimulated with TLR agonist, including R848 (InvivoGen #tlrl-r848) and ODN2395 (InvivoGen #tlrl-2395), and incubated at 37° C. with 5% $CO_2$ for 18 hr. Supernatants of cell culture medium were collected for TNF-α measurements.

THP1/XBlue/MD2/CD14 Cell Line

THP1/XBlue/MD2/CD14 cell line was derived from the human monocytic THP1 cell line and purchased from InvivoGen. Cells were cultured in RPMI1640 containing 10% heat inactivated FBS and antibiotic at 37° C. with 5% $CO_2$.

In Vitro Assays

To investigate the effects of anti-TLR4 antibody (HTA125, BioLegend #312814) and anti-MD2 antibody (18H10, ThermoFisher #MA5-33351) on TREML1 ECD binding to THP1/XBlue/MD2/CD14 cells, cells were pretreated with anti-MD2 antibody, anti-TLR4 antibody, IgG control, or a combination for 15 min at 37° C. with 5% $CO_2$. After antibodies treatments, cells were treated with TREML1 ECD (10 ug/ml) and incubated for 1 hours. Cells were washed with PBS containing 1% FBS and stained with AF647-anti-human TREML1 antibody, followed by flow cytometric analysis.

NF-κB Activation in THP1/XBlue/MD2/CD14 Cells

To investigate the effects of anti-TLR4 antibody and anti-MD2 antibody on TREML1 ECD-triggered TLR response, THP1/XBlue/MD2/CD14 cells were pretreated with anti-TLR4 antibody, anti-MD2 antibody, or IgG control for the indicated groups and incubated for 15 minutes at 37°

C., 5% $CO_2$. After pretreatments, THP1/XBlue/MD2/CD14 cells were stimulated by TREML1 ECD (10 ug/ml) and seeded at a concentration of $1\times10^6$ cells/ml (200 ul per well) into wells of a 96-well plate for 18 hr at 37° C., 5% $CO_2$. To determine the NF-κB activation, the supernatants of culture medium were collected and assessed with QUANTI-Blue™ reagent (InvivoGen) according to the manufacturer's instructions.

Cytokine Analyses

Cell supernatants and plasma samples were harvested and stored at −80° C. Human TNFα concentrations were detected using TNF-α DuoSet ELISA kit (R&D #DY210) according to manufacturer's instructions. Signals were developed using 3,3',5,5'-tetramethylbenzidine and the absorbance of 450 nm was detected with a microplate reader.

Flow Cytometric Analysis

The cells were resuspended in PBS containing 1% FBS at a density of $2\times10^6$ cells/ml and non-specific bindings of Abs were blocked using Human Fc Block (BD Biosciences #564220) at room temperature for 10 min. AF647-anti-human TREML1 (clone 268420) (R&D #FAB2394R) antibody was used as a detection antibody of TREML1 binding to cell surface. Dead cells were excluded according to Fixable Viability Stain 780 (FVS780) (BD Horizon #565388) staining. Binding analysis was performed on a CytoFLEX Flow Cytometer (Beckman Coulter) and the collected data were analyzed using Kazula software.

Mouse Bone Marrow Derived Dendritic Cell Generation

Femurs and tibiae were harvested from female C57BL/6 mice and extra muscle tissues were removed. Bones were disinfected in 70% ethanol, then rinsed with RPMI-1640 medium, and both ends were cut to flush out the bone marrow with RPMI-1640 medium using 26 G needle syringes. To disperse cell clumps, bone marrow suspension was pipetted in-and-out several times and washed twice with RPMI-1640 medium by centrifugation. The R10 culture medium was comprised of RPMI1640 with antibiotic, 10% inactive Fetal Bovine Serum, and 2-mercaptoethanol (50 μM, Sigma USA). At day 0, after cell counting, the leukocytes were seeded at a concentration of $2\times10^6$ cells/10 ml R10 medium containing 200 U/ml rmGM-CSF in sterile 10 mm diameter Petri dish and incubated at 37° C. with 5% $CO_2$. At day 3, another 10 ml of R10 medium containing 200 U/ml rmGM-CSF was added. At days 6, one half of the supernatant was taken out and centrifuged to collect cell pellet, which was resuspend in original plate with 10 ml of R10 medium containing 200 U/ml GM-CSF. At day 8, non-adherent cells were collected by gentle pipetting and centrifuged at 300 g for 5 min. To obtain purer dendritic cells, the population of macrophages (F4/80$^{high}$) was removed with Anti-F4/80 MicroBeads UltraPure (130-110-443, Miltenyi Biotec, Bergisch Gladbach, Germany) following the manufacturer's instructions. Briefly, cell pellet was resuspended and mixed well in MACS buffer with Anti-F4/80 MicroBeads UltraPure. This mixture was incubated for 15 min in the dark in 4° C. After washing cells with MACS buffer, cells were resuspended in MACS buffer, filtered with 30 μm nylon mesh, and added to the MACS buffer rinsed column to separate F4/80$^+$ cells. Unlabeled cells were collected and washed with R10 medium. To freeze the cells, cell pellet was counted and resuspended at a concentration $1\times10^7$ cell in 2 ml CELLBANKER2 (#11891, ZENOAQ) per cryopreservation vial and stored at −80 degree Celsius.

BMDCs were thawed for the DC maturation experiments. These cells were seeded at $1\times10^6$ cells/2 ml in R10 medium containing 200 U/ml rmGM-CSF in wells of a 6-well tissue culture dish and cultured to recover the cell viability at 37° C. with 5% $CO_2$. After 6 hr, BMDCs were treated with various fragments of mTREML1 protein and cultured in 37° C. with 5% $CO_2$. On the next day, resuspended cells were collected and analyzed by flow cytometry.

Cells were centrifuged at 1800 rpm for 3 min in PBS containing 1% FBS and 0.1% sodium azide (PBSBA), and then divided at a concentration of $1\times10^5$ cells/100 ul PBSBA in flow tube. Before staining the surface marker of DC, cells were treated with mouse Fc blocker to avoid antibody non-specific binding at room temperature for 30 min. Cells were incubated with the following antibodies: PE anti-mouse CD11c Antibody (BioLegend #117308), Brilliant Violet 421™ anti-mouse I-A/I-E Antibody (BioLegend #107631), BV786 Rat Anti-Mouse CD40 (BD #140891), Alexa Fluor® 488 anti-mouse CD86 Antibody (BioLegend #105018), or PE/Dazzle™ 594 anti-mouse CD80 Antibody (BioLegend #104737) for 30 min at 4° C. After PBSBA washing, samples were analyzed using the CytoFlex flow cytometer with the CytExpert software.

Mice

All genetically wild-typed experimental BALB/c and C57BL/6 mice were purchased from National Laboratory Animal Center (Taiwan). The experimental procedures of all animal experiments were compliant with the regulations of local Institutional Animal Care and Use Committee (IACUC).

Tumor Studies

For the establishment of syngeneic murine colon cancer models, BALB/c mice were subcutaneously injected in the back with $3\times10^5$ CT26 cells per mouse. When the volume of the inoculated tumor reached 30-100 mm$^3$, mice were randomly divided into cohorts for different treatments. Tumor antigen-vaccines were subcutaneously administered according to the indicated time schedule. During each animal study, tumor dimensions were monitored with caliper measurements, and the tumor volumes were calculated using the equation: v=π/6 (length)×(width), wherein length is the longest diameter of the tumor and the width is the shortest diameter. If the size of tumor burden exceeds 3000 mm$^3$, the mice were considered dead in the survival study and euthanized using $CO_2$ or cervical dislocation.

Embodiments of the invention have been described using a limited number of examples. One skilled in the art would appreciate that these examples are for illustration only and that other modifications and variations are possible without departing from the scope of the invention. Therefore, the scope of protection should be limited only by the attached claims.

What is claimed is:

1. A method of boosting an immune response against cancer cells in a subject in need thereof, wherein the method comprises:

administering a pharmaceutical composition comprising a cancer vaccine and a soluble TREM-like transcript-1 (TREML1) to the subject, the soluble TREML1 comprising a TREML1 extracellular domain (ECD) or TREML1 stalk polypeptide; and inhibiting growth of the cancer cells, wherein the inhibition of the growth of the cancer cells is higher as compared to the pharmaceutical composition comprising the cancer vaccine without the soluble TREML1, thereby boosting an immune response against the cancer cells in the subject.

2. The method according to claim 1, wherein the TREML1 ECD or TREML1 stalk polypeptide is obtained from human or mouse TREML1.

3. The method according to claim 1, wherein the TREML1 ECD or TREML1 stalk polypeptide comprises the amino-acid sequence of SEQ ID NO: 1, SEQ ID NO:2, SEQ ID NO:3, or SEQ ID NO:4.

4. The method according to claim 1, wherein the pharmaceutical composition further comprises Toll-like receptor (TLR) agonist.

5. The method according to claim 4, wherein the TLR agonist is a lipopolysaccharide, a heat shock protein, a fibrinogen, a heparan sulfate fragment, a hyaluronic acid fragment, a CpG oligodeoxynucleotide, 4-amino-2-(ethoxymethyl)-α,α-dimethyl-1H-imidazo[4,5-c]quinoline-1-ethanol (R848), or an opioid drug.

6. The method according to claim 1, wherein the cancer vaccine comprises an antigen.

7. The method according to claim 6, wherein the antigen is a marker of a cancer.

8. The method according to claim 7, wherein the cancer cells are from a cancer selected from the group consisting of colorectal cancer, breast cancer, lung cancer, melanoma, hepatoma, head and neck cancers, squamous cell carcinomas of the lung, ovarian cancer, uterine cancer, prostate cancer, gastric carcinoma, cervical cancer, esophageal carcinoma, bladder cancer, kidney cancer, brain cancer, bone cancer, pancreatic cancer, skin cancer, cutaneous or intraocular malignant melanoma, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, esophagus cancer, small intestine cancer, endocrine system cancer, thyroid gland cancer, parathyroid gland cancer, adrenal gland cancer, sarcoma of soft tissue, urethra cancer, penis cancer, chronic or acute leukemias, solid tumors of childhood, lymphocytic lymphoma, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, medulloblastoma pilomatrixomas, endometrial cancer, multiple myeloma, and T-cell lymphoma.

9. The method according to claim 8, wherein the chronic or acute leukemias comprise acute myeloid leukemia, chronic myeloid leukemia, acute lymphoblastic leukemia, or chronic lymphocytic leukemia.

10. The method according to claim 1, wherein the method enhances an innate immune response in the subject.

11. The method according to claim 1, wherein the method enhances an adaptive immune response in the subject.

12. A method of enhancing a TLR-induced activation of cells, wherein the method comprises;

administering a pharmaceutical composition comprising a TLR agonist and a soluble TREML1 to the cells, the soluble TREML1 comprising TREML1 ECD or TREML1 stalk polypeptide; and inducing a higher level of TLR-induced activated cells as compared to the pharmaceutical composition comprising the TLR agonist without the soluble TREML1, thereby enhancing a TLR-induced activation of cells.

13. The method according to claim 12, wherein the activation comprises activation of monocytes.

14. The method according to claim 13, wherein the activation of monocytes comprises secretion of NF-κB or TNF-α.

15. The method according to claim 12, wherein the activation of cells comprises dendritic cell maturation.

* * * * *

SEQUENCE LISTING

<160> NUMBER OF SEQ ID NOS: 5

<210> SEQ ID NO 1
<211> LENGTH: 147
<212> TYPE: PRT
<213> ORGANISM: homo sapiens

<400> SEQUENCE: 1

```
Gln Gly Ile Val Gly Ser Leu Pro Glu Val Leu Gln Ala Pro Val Gly
1               5                   10                  15

Ser Ser Ile Leu Val Gln Cys His Tyr Arg Leu Gln Asp Val Lys Ala
            20                  25                  30

Gln Lys Val Trp Cys Arg Phe Leu Pro Glu Gly Cys Gln Pro Leu Val
        35                  40                  45

Ser Ser Ala Val Asp Arg Arg Ala Pro Ala Gly Arg Arg Thr Phe Leu
    50                  55                  60

Thr Asp Leu Gly Gly Gly Leu Leu Gln Val Glu Met Val Thr Leu Gln
65                  70                  75                  80

Glu Glu Asp Ala Gly Glu Tyr Gly Cys Met Val Asp Gly Ala Arg Gly
                85                  90                  95

Pro Gln Ile Leu His Arg Val Ser Leu Asn Ile Leu Pro Pro Glu Glu
            100                 105                 110

Glu Glu Glu Thr His Lys Ile Gly Ser Leu Ala Glu Asn Ala Phe Ser
            115                 120                 125

Asp Pro Ala Gly Ser Ala Asn Pro Leu Glu Pro Ser Gln Asp Glu Lys
    130                 135                 140

Ser Ile Pro
145
```

<210> SEQ ID NO 2
<211> LENGTH: 155
<212> TYPE: PRT
<213> ORGANISM: Mus musculus

<400> SEQUENCE: 2

```
Asp Ser His Pro Glu Val Leu Gln Ala Pro Val Gly Ser Ser Ile Leu
1               5                   10                  15

Val Gln Cys His Tyr Arg Leu Gln Asp Val Arg Ala Leu Lys Val Trp
            20                  25                  30

Cys Gln Phe Leu Gln Glu Gly Cys His Pro Leu Val Thr Ser Ala Val
        35                  40                  45

Asp Arg Arg Ala Pro Gly Asn Gly Arg Ile Phe Leu Thr Asp Leu Gly
    50                  55                  60

Gly Gly Leu Leu Gln Val Glu Met Val Thr Leu Gln Glu Glu Asp Thr
65                  70                  75                  80

Gly Glu Tyr Gly Cys Val Val Glu Gly Ala Ala Gly Pro Gln Thr Leu
                85                  90                  95

His Arg Val Ser Leu Leu Val Leu Pro Pro Val Pro Gly Pro Arg Glu
            100                 105                 110

Gly Glu Glu Ala Glu Asp Glu Lys Glu Thr Tyr Arg Ile Gly Thr Gly
            115                 120                 125

Ser Leu Leu Glu Asp Pro Ser Leu Asp Pro Ser Ala Ser Ala Gly Pro
    130                 135                 140

His Glu Phe Arg Arg Arg Glu Asn Ser Ile Pro
145                 150                 155
```

```
<210> SEQ ID NO 3
<211> LENGTH: 41
<212> TYPE: PRT
<213> ORGANISM: Homo sapiens

<400> SEQUENCE: 3

Ile Leu Pro Pro Glu Glu Glu Glu Glu Thr His Lys Ile Gly Ser Leu
1               5                   10                  15

Ala Glu Asn Ala Phe Ser Asp Pro Ala Gly Ser Ala Asn Pro Leu Glu
            20                  25                  30

Pro Ser Gln Asp Glu Lys Ser Ile Pro
        35                  40

<210> SEQ ID NO 4
<211> LENGTH: 44
<212> TYPE: PRT
<213> ORGANISM: Mus musculus

<400> SEQUENCE: 4

Glu Gly Glu Glu Ala Glu Asp Glu Lys Glu Thr Tyr Arg Ile Gly Thr
1               5                   10                  15

Gly Ser Leu Leu Glu Asp Pro Ser Leu Asp Pro Ser Ala Ser Ala Gly
            20                  25                  30

Pro His Glu Phe Arg Arg Arg Glu Asn Ser Ile Pro
        35                  40

<210> SEQ ID NO 5
<211> LENGTH: 20
<212> TYPE: PRT
<213> ORGANISM: Artificial Sequence
<220> FEATURE:
<223> OTHER INFORMATION: Synthetic

<400> SEQUENCE: 5

Glu Glu Glu Glu Glu Thr Tyr His Ser Pro Ser Tyr Val Tyr His Gln
1               5                   10                  15

Phe Glu Arg Arg
            20
```